United States Patent [19]

Beck

[11] Patent Number: 4,979,508

[45] Date of Patent: Dec. 25, 1990

[54] APPARATUS FOR GENERATING PHOSPHENES

[76] Inventor: Stephen C. Beck, 1350 Summit Rd., Berkeley, Calif. 94708

[21] Appl. No.: 48,082

[22] Filed: Apr. 11, 1987

Related U.S. Application Data

[63] Continuation of Ser. No. 658,888, Oct. 9, 1984, Pat. No. 4,664,117.

[51] Int. Cl.$^5$ .............................................. A61N 1/00
[52] U.S. Cl. .................................... 128/419 R; 600/26
[58] Field of Search ................ 128/419 R, 420.5, 421, 128/422, 423 R, 791, 793; 600/26, 27; 623/4, 66; 340/407

[56] References Cited

U.S. PATENT DOCUMENTS

| | | | |
|---|---|---|---|
| 2,703,344 | 3/1955 | Anderson | 340/407 |
| 3,699,970 | 10/1972 | Brindley et al. | 623/66 |
| 4,254,776 | 3/1981 | Tonie et al. | 128/421 |

Primary Examiner—William E. Kamm
Attorney, Agent, or Firm—Ashen Martin Seldon Lippman & Scillieri

[57] ABSTRACT

The apparatus and method produce visual sensations by applying low voltages through conductive electrodes to the outside of a person's head, for transmission by natural mechanisms to the nervous system—to entertain or inform a sighted person, or to help a blind person to locate nearby objects.

As to entertainment, the apparatus generates various waveshapes, and an operator directs one or more to the electrodes. The operator also manually varies waveshape parameters such as frequency, amplitude, duty cycle and dc bias—or controls them with automatic sweep devices at selected sweep rates. Various wavetrains are combined at the electrodes or in the person's head for more-elaborate effects. The electrode wavetrains or necessary control signals are also received for playback.

As to information, the apparatus produces coded patterns or even rough analogs of normal visual scenes. As to aiding the blind, the apparatus responds to a sonar signal by placing phosphenes in the perceived visual field roughly where a normal person would see nearby objects.

3 Claims, 6 Drawing Sheets

Electrode Disc Detail

TRIANGULATION SCHEME FOR
2 ULTRASONIC SENSORS.

APPARATUS FOR GENERATING PHOSPHENES

This is a divisional of copending application 658,888, filed on Oct. 9, 1984, and issued on May 12, 1987, as U.S. Pat. No. 4,664,117.

BACKGROUND

1. Field of the Invention

This invention relates generally to phosphenes, and more particularly to the production of entertaining, informative or useful visual sensations by application of electrical signals to the outside of a person's head.

2. Prior Art

During the last twenty-two years several technical publications have described research and experimentation with phosphenes — visual sensations experienced in the absence of normal visual stimulus. Such sensations may be induced by mechanical pressure on closed eyelids, by impact to the body, by various diseases or drugs, and particularly by electrical stimulation of the nervous system. The electrical approach has taken two forms. Some medical researchers have explored the implantation of electrodes directly in the optical center of the human brain, for purposes such as aiding the blind. One rather advanced paper on this subject is Marg et al., "Design for a phosphene visual prosthesis," 19 Brain Research 502-10 (Elsevier Publishing, Amsterdam 1970), citing a dozen other articles of the same era.

Based in part upon prior published work, Marg proposes implantation of a solid-state logic system, inductive receiver, and signal-distribution unit in a hole in the cranium, just inside the flesh and skin at the upper rear of the patient's head. Five hundred brain-implanted electrodes would be fed signals from this unit, which would in turn receive information from a complementary apparatus worn outside the patient's cranium.

The latter apparatus would be adapted to couple video-like signals (derived from a sort of video camera) and radio-frequency electrical power inductively through the flesh and skin to the inner unit. Among the spectacular assignments of these devices would be a custom mapping of the implanted electrodes to the patient's visual field, and a custom tuning of their amplitude response to the sensitivity response across the patient's visual field.

It will be apparent that such devices would be enormously expensive, somewhat hazardous to install, and possibly even subject to radio interference.

The other form of research into electrically produced phosphenes has focused upon their generation by conductive electrodes applied to the exterior of the body (generally of the head), with reliance upon natural mechanisms of conduction to the nervous system.

A summary of some such work is provided by Oster, "Phosphenes," 222 Scientific American 83—87 (Feb, 1970). Oster mentions some of his own research into the relationship between observed flickering of externally-induced phosphenes and frequency of the input voltages. Oster observed, as have other workers, a cutoff of direct phosphene generation above about 40 Hz.

Among Oster's experiments was the use of two electrically independent generators and four electrodes; with this equipment he applied pulses of two different frequencies simultaneously. Oster's interest in this experiment was to observe the effects of beats between the two frequencies. The beats produced phosphenes, even though each of the pulse trains was at a frequency above the cutoff frequency and could therefore produce no phosphenes by itself.

It is significant to note that Oster's use of four electrodes was for the purpose of mixing frequencies within the subject's head. He does not suggest any particular electrode placement for this purpose, and does not suggest any other reason to use more than two electrodes.

A more detailed first-hand report is given by Knoll et al,, "Die Reproduzierbarkeit von elektrisch angeregten Lichterscheinungen (Phosepene) bei zewei Versuchs personen innehalb von 6 Monaten," 7 Elektromedizin No. 4 (Institut fur Technische Elektronik der Technischen Hochschule, Munich 1962).

Knoll and his associates stimulated their research subjects electrically with pulses of rectangular waveshape, applied through electrodes at the temples or over the eyes. The amplitude was between 0.5 and 3.5 volts, the frequency was systematically varied from zero to 100 Hz, and the pulse duty cycle (ratio of "on" time to total time) was similarly varied between 2:1 and 1:20. The researchers plotted the sketches of different phosphene patterns reported by their subjects for dozens of different combinations of frequency and pulse duty cycle, covering the ranges stated above.

Their resulting chart shows that most phosphene activity occurs below an excitation frequency of 40 Hz. A few patterns were observed at higher frequencies, but my own experience has shown that a sudden and abrupt cutoff does occur at 40 Hz. The types of phosphene patterns vary in a complicated way with pulse frequency and duty cycle.

For example, at 20 Hz there is a definite progression of sensation types with increasing pulse duty cycle. At pulse ratios of 1:1 the patterns are round or flower-like. As the ratio decreases (i. e., as the pulses become narrower) the patterns change to lines, both straight and wavy. At very low values, such as 1:14, the pattern becomes radial or star-like. At other ratios there are pointillistic patterns.

For each of Knoll's subjects, sensation types bore a fixed relationship to frequency and pulse duty cycle — the correlation was reproducible even over six months. As between different subjects, however, and as I too have found, the relationships are not always well correlated.

Knoll has also reported on the effects of administering to the research subjects certain chemicals — such as a very small dose of a hallucinogenic drug — upon the phosphenes. Knoll et al., "Effects of Chemical Stimulation of Electrically-Induced Phosphenes on their Bandwidth, Shape, Number and Intensity," 23 Confin Neurology 201—26 (S. Karger, Basil, Switzerland 1963).

All of the various reported efforts with externally-induced phosphenes have been directed to basic research, with the goal of advancing the understanding of neurological phenomena. The published reports do not indicate any direct practical applications of externally-induced phosphenes.

SUMMARY OF THE DISCLOSURE

My invention provides direct practical uses of phosphenes produced by external conductive application of electrical pulses. Most of the applications of my invention depend upon the natural bodily mechanisms of electrical conduction from the skin to the nervous system.

Among the practical uses provided by my invention are entertainment, information transfer, and aid to the blind.

For entertainment purposes, one embodiment of my invention is a phosphene generator for producing visual sensations in a person. The generator includes some means for generating substantially rectangular voltage wavetrains, as used in the experiments of Knoll and others.

My apparatus, however, uses a much wider range of impulse waveforms than reported by Knoll. In particular, the embodiment now under discussion also includes means for generating substantially triangular, sinusoidal, and ramp-shaped voltage wavetrains, as well as rectangular.

Also provided is some means for selecting at least one of these wavetrains — as varied by the several controls mentioned above — for application to the person who will perceive the phosphenes.

With a sine or triangle wave, the visual effect is a "fade in ... fade out" with soft, gradual edges. The triangle waveform, however, produces a brief flash or point of light at its peaks. The square wave produces the most dramatic effects: bright flashes with a staccato or punctuated effect.

This embodiment also includes some means for varying the pulse duty cycle of the rectangular wave train, and some means for varying the frequency or amplitude (or both) of any of the wavetrains, and some means for applying a dc bias voltage to any of the wavetrains. All of these varying devices are advantageously operable manually by a person who controls, or "plays" or "performs on" this embodiment of my invention.

By varying the dc bias voltage (or the duty cycle, which has the incidental effect of varying the average voltage) I can move the images toward the left or the right side of the viewer's field of sight. A balanced waveform centers the images. Thus "stereo" sweep visual effects may be obtained.

There are remarkable frequency-sensitive effects. At low frequencies from less than 1 Hz to about 20 Hz the phosphene image is distinct, and it is singular. Between 20 and 30 Hz the singularity changes into more of a field or texture effect, with a single phosphene pattern giving way to micropatterns. Then between 30 and 40 Hz the entire field of view explodes with a myriad of detailed micropatterns.

The higher-frequency patterns are the most interesting from a visual standpoint. Scintillating dots, or moire patterns, paisley-like forms, brilliant colors, and much animation all seem to be at a maximum in this higher frequency range. As the frequency is raised from the singularity range to the micropattern range, a central, pulsing sphere will shatter into thousands of colored bubbles.

Finally, the embodiment necessarily has some means for applying these varied wavetrains to the person.

It will be understood that "the person" now refers not to a "subject", as in the neurological research work discussed earlier, but rather to a person who seeks an esthetic or otherwise entertaining or relaxing sensory experience — analogous to, for example, watching a laser show or a picture show, or listening to music, or having a massage. Such a person may be a consumer who has obtained equipment for use at home, or perhaps a customer who has gone to a commercial establishment (analogous to a movie theater) for a time of entertainment.

It is preferable to provide some means for automatically controlling the variables of frequency, duty cycle, amplitude and dc bias mentioned above. These means for varying frequency, duty cycle, amplitude and dc bias may sweep automatically through a predetermined range of each of the parameters, at a particular sweep rate or rates.

Such devices may be manually operable to control the sweep rate or rates. I have found that phosphene observation is highly compatible with enjoyment of various acoustic or auditory phenomena, such as music, poetry, or natural sounds such as wind, falling water, laughter, and so forth.

In fact, I have found it very worthwhile to present a concert of phosphenes in conjunction with music of many different kinds. With practice the operator of the phosphene generator can develop an ability to interpret (or complement) music or other auditory phenomena in phosphenical terms. In one such concert, I operated or played upon the phosphene generator as part of a trio that also included a guitarist, playing on a processed electronic guitar, and a percussionist. The musicians and I were wired to the phosphene generator, in a parallel configuration with audience members.

After seating the guests, we placed the electrodes on each guest's temples — along with a small quantity of an electrolytic paste that is commercially available under the name "Stimugel". This substance improves conductivity into the skin.

The lighting was a subdued red light to help begin the dark-adaptation process. As a prelude there was a verbal recitation of the phosphene phenomenon, including a reminder that the guests could easily remove the electrodes at any time if they began to feel any discomfort from the electrical impulses. (Many of the guests were not at all bothered by the minor shock, similar to a small needle prick, and in fact some seemed to relish the sensation.)

The music then began, still as part of the prelude, while the guests became dark adapted. After about ten minutes the second movement commenced. Some of the guests reported perception of the effect immediately, while others required several more minutes.

The highlights of this performance were the interplay between the musicians and the operator of the phosphene generator. As the music ranged from slow adagios and subdued modalities to lively, quick andantes and allegro tempos, I varied the phosphene frequency and waveform accordingly. Sometimes the musicians would follow the tempo set by the phosphenes, and at other times I would follow their tempo.

About one in ten individuals saw no effects at all. Over forty percent reported quite vivid phosphenes, especially as dark adaptation improved later in the piece. Guests were freely encouraged to describe their perceptions verbally, and many times several guests simultaneously spoke up about "the blue lines" or "all those colored dots."

Duration of each guest's session was limited to about thirty minutes. None reported detrimental or negative aftereffects. The musicians and I gave six such concerts in direct succession, thus being wired to the phosphene generator for a total of three hours; we incurred minor electrode burns on the temples, but no adverse effects upon our vision even after the total accumulated exposure.

Alternatively, or in addition, to manual sweep control, my invention may be made to adjust the wavetrain parameters (or their sweep rates) in response to some external input.

In particular, since acoustic phenomena can be worthwhile in conjunction with phosphenes, the embodiment of my invention now under discussion is advantageously provided with some means for deriving or receiving electrical signals that are related to the characteristics of acoustic phenomena. These acoustic-phenomena-related signals are connected to control the variation of frequency, duty cycle, amplitude or dc bias of the phosphene-generating wavetrains.

A second embodiment of my invention is similarly a phosphene generator for producing visual sensations in a person. As in the first embodiment, there are some means for generating voltage wavetrains, and these wavetrains (by definition) have parameters that include frequency, amplitude, and dc bias. There are of course some means for applying the voltage wavetrains to the person. This embodiment, however, does not necessarily have manually controllable devices for varying the wavetrain parameters.

It does have some means for deriving or receiving electrical signals related to the characteristics of acoustic phenomena, and some means for applying these signals to control at least one of the wavetrain parameters. In other words, this embodiment of my invention provides the automatic modulation of wavetrain parameters that is particularly suited for observing phosphenes in combination with listening to auditory phenomena — but it does not necessarily provide the manual modulation of such parameters.

Thus the first embodiment of my invention provides, in essence, a phosphenical instrument, akin to a musical instrument, which offers a user or "player" (or perhaps "phosphenist" an opportunity to perform an act of esthetic creation. The second embodiment provides, in essence, an automatic device for creating a phosphenic interpretation of an acoustic occurrence — for instance, a phosphenic interpretation of a musical concert. (It should be noted that the resulting interpretation can be enjoyed either separately or while listening to the music.)

The two embodiments may be joined. however, in a phosphene generator in which both manual and automatic adjustment of the wavetrain parameters is provided. This system permits an advanced player upon the manual controls to vary or modulate the effects of the music (or other auditory phenomenon) upon the phosphenes. The musical input becomes one more interactive tool of the system.

Two different frequencies, or several different frequencies, may be used for the stimulating wavetrains. Various frequencies may be applied to the several controls in lieu of, or in conjunction with, manual adjustment. Remarkably enough, the phosphene "space" when used in such ways is an extremely rich medium. Such complex waveform combinations produce a monumentally variable choice of sensory experiences, limited only by the creativity of the person who selects the acoustic inputs and molds them by controlling the variables in the ways just outlined.

A third embodiment of my invention is a phosphene generator coupled with a recorder. This combination has some means for storing the varying wavetrain and later playing back the varying wavetrain for application to a person.

A fourth embodiment of my invention is a programmable phosphene generator. This embodiment is related to the third embodiment in that both provide the capability of repeating a series of phosphene stimuli. In this case, however, it is the control signals rather than the voltage wavetrains that are recorded. The combination includes some means for storing and later playing back the control signals.

A fifth embodiment of my invention is a phosphene generator for aiding a blind person to determine the positions or other characteristics of nearby objects. This embodiment includes some means for deriving signals that are related to the positions or other characteristics of such objects. Suitable automatic sensor apparatus for this purpose would be a sonar or radar system — or a device analogous to a video camera, such as described in the work by Marg et al. mentioned earlier.

This embodiment of my invention also includes some means for converting the sensor signals into related voltage waveforms suitable for conductive application to the outside of a person's head. This signal-processing stage must make the transformation between (1) the representation of true spatial relations that is implicit in the sensor signals and (2) the representation of spatial relations that is implicit in the phosphene-stimulating wavetrains, as they produce perceptions in the blind person's subjective "visual field."

Preferably the transformation should be accomplished in such a way that these two representational systems are made consistent, so that the phosphenes will "appear" to the blind person in the "proper" locations. (For simplicity the representation could be one-dimensional, giving only left-vs.-right information, and the sensors could be made maximally sensitive in a plane parallel to the "equator" of the person's head. The user could educe elevational information by tilting of the head.) My invention does encompass, however, a system in which the blind user must interpret the appearance of the phosphenes to obtain locational information.

For example, the center of the apparent visual field might represent leftward objects, and either or both peripheries of the apparent visual field might represent rightward objects. As another example, radial patterns might represent leftward objects, nonradial linear patterns might represent central objects, and round flower-like patterns might represent rightward objects. Such representational systems may be somewhat awkward at first, but might have the advantage of requiring no long-term dc component of the voltages applied to the person's body, therefore avoiding possible adverse electrolytic effects to the nervous system.

More usefully, punctuate or pointillistic patterns might represent more remote objects while continuous textural patterns might represent nearer objects.

In addition to the automatic signal-deriving apparatus and the signal-converting apparatus, this embodiment of my invention also includes some means for application of the voltage waveforms to the person's body. My invention is unlike the brain implantations described in the literature, which rely — as will be recalled — upon inductive coupling through the scalp, and upon wires running to electrodes on the brain. Rather, the waveform-application means of my invention rely upon conductive application to the person's body, through electrodes attached to the outside of a person's head, and upon transmission to the nervous system solely by naturally occurring mechanisms with the person's body.

A sixth embodiment of my invention is a phosphene generator for presentation of scene images to a person. Relative to the fifth embodiment just discussed, this sixth embodiment is in a sense a generalization — in that (1) the spatial representations should be two-dimensional rather than only one-dimensional, and (2) the spatial representations need not be of objects contemporaneously near the person but may be recorded. The recording may be accompanied by an audible story line or the like.

A seventh embodiment of my invention is a method of producing visual images for entertainment or information. The method includes at least three steps: (1) providing a sequence of signals that is related to an entertaining or informative programme of visual sensations, (2) converting the signals into a sequence of related voltage waveforms suitable for application to the outside of a person's body; and (3) applying the signals to a conductive-electrode headset worn by the person, for transmission solely by naturally occurring mechanisms with the person's body to produce in that person the entertaining or informative programme of visual sensations.

An eighth embodiment is a method related to that of the seventh embodiment, but more specifically directed to informational images which may not be preplanned. Such informational images might conceivably not come under the concept of a programme. In this case the visual sensations are simply a sequence, not necessarily a programme.

All of the foregoing operational principles and advantages of the present invention will be more fully appreciated upon consideration of the following detailed description, with reference to the appended drawings, of which:

BRIEF DESCRIPTION OF THE DRAWINGS

FIG. 7 also serves as an electrical block diagram of a phosphene generator for use in aiding the blind, according to the fifth embodiment of my invention. FIG. 7 further serves an electrical block diagram of a phosphene generator for presenting two-dimensional scene information, according to the sixth embodiment of my invention.

DETAILED DESCRIPTION OF THE PREFERRED EMBODIMENTS

Figure 1:
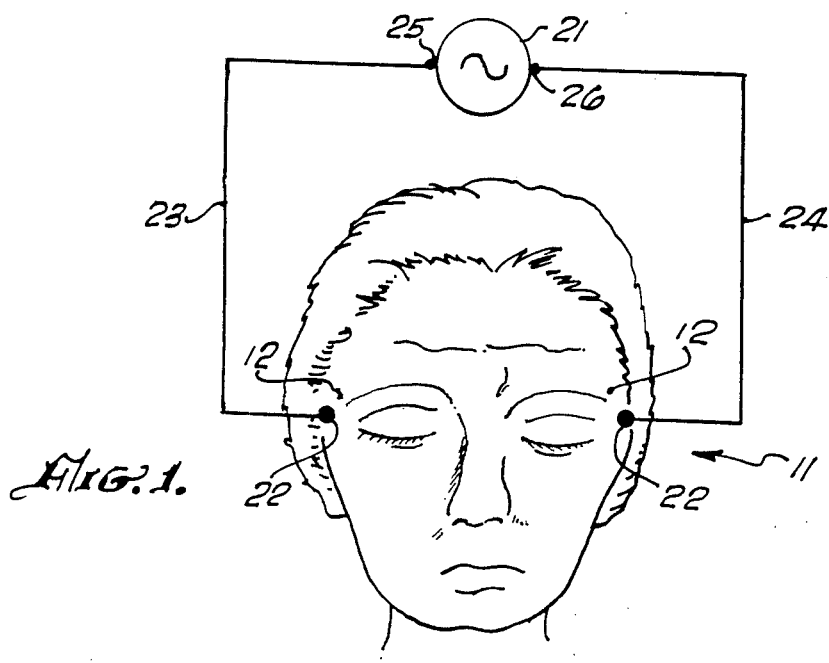
FIG. 1 is in part a fanciful elevation and in part an electrical schematic depicting the application of electrical signals to the outside of a person's body in accordance with several of the embodiments of my invention.

As shown in FIG. 1, my invention makes electrical contact to the temples 12 of a user 11, just behind the corner of the eye. A pair of external electrodes 22 is attached to the temples 12, and these electrodes 22 are connected by leads 23 and 24 to terminals 25 and 26 of a wavetrain-producing apparatus 21. Other contact points can be used too. DO NOT TRY TO REPRODUCE THE HUMAN CIRCUIT USED IN MY INVENTION UNLESS YOU UNDERSTAND HOW TO ISOLATE THE USER 11 FULLY AND COMPLETELY AGAINST ELECTROCUTION!

The apparatus 21 has an output impedance that optimizes the electrical impulses conducted into the head of the person 11. Suitable voltage and current limiting circuitry is also included to protect the user from excessive currents or voltages that could prove injurious or fatal. Voltage is limited to two volts, and current to less than ten microamperes.

Figure 2:
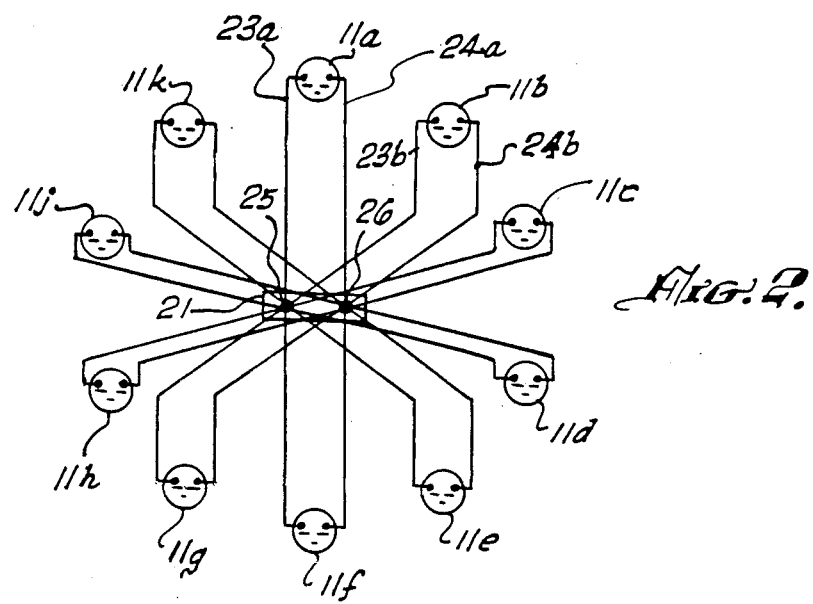
FIG. 2 is an electrical schematic depicting the application of electrical signals to the outsides of the bodies of several people at the same time, in accordance with several of the embodiments of my invention.

As shown in FIG. 2, a group of people 11a through 11k may be wired in parallel. One approach to doing so involves, as illustrated, replicating the leads 23 and 24 of FIG. 1 as leads 23a and 24a, 23b and 24b, etc. These lead pairs all connect to the common terminals 25 and 26 of the wavetrain-producing apparatus 21. For such occasions the current should be made adjustable. It may be preferable, however, to provide separate current limiting (not illustrated) for each user.

The parallel circuit feeds the same impulses to all the user's heads simultaneously. This configuration is to be distinguished from a series circuit, in which the source signal passes first through one viewer, then the next, and so on. A series hookup has the undesirable characteristics that a much greater voltage must be used, and if one viewer removes the electrode set the circuit is broken for all.

As previously mentioned there are many different kinds of phosphenes to be seen by a user connected to a suitable wavetrain-producing apparatus in the manner illustrated. Some phosphenes are simply specks or dots of bright light, usually ruby red or deep blue, scintillating against a black background. Others assume more specific forms such as wavy lines with a vertical, horizontal or diagonal orientation. Still others are distinctly radial or centripetal. The coloring of phosphenes encompasses a wide range of hues and luminosity. After the dark adaptation period the first phosphenes observable are usually faint and pale, lacking much color saturation. Later, however, the coloration becomes more vivid. Pale colors give way to richer, more saturated colors.

Figure 3:
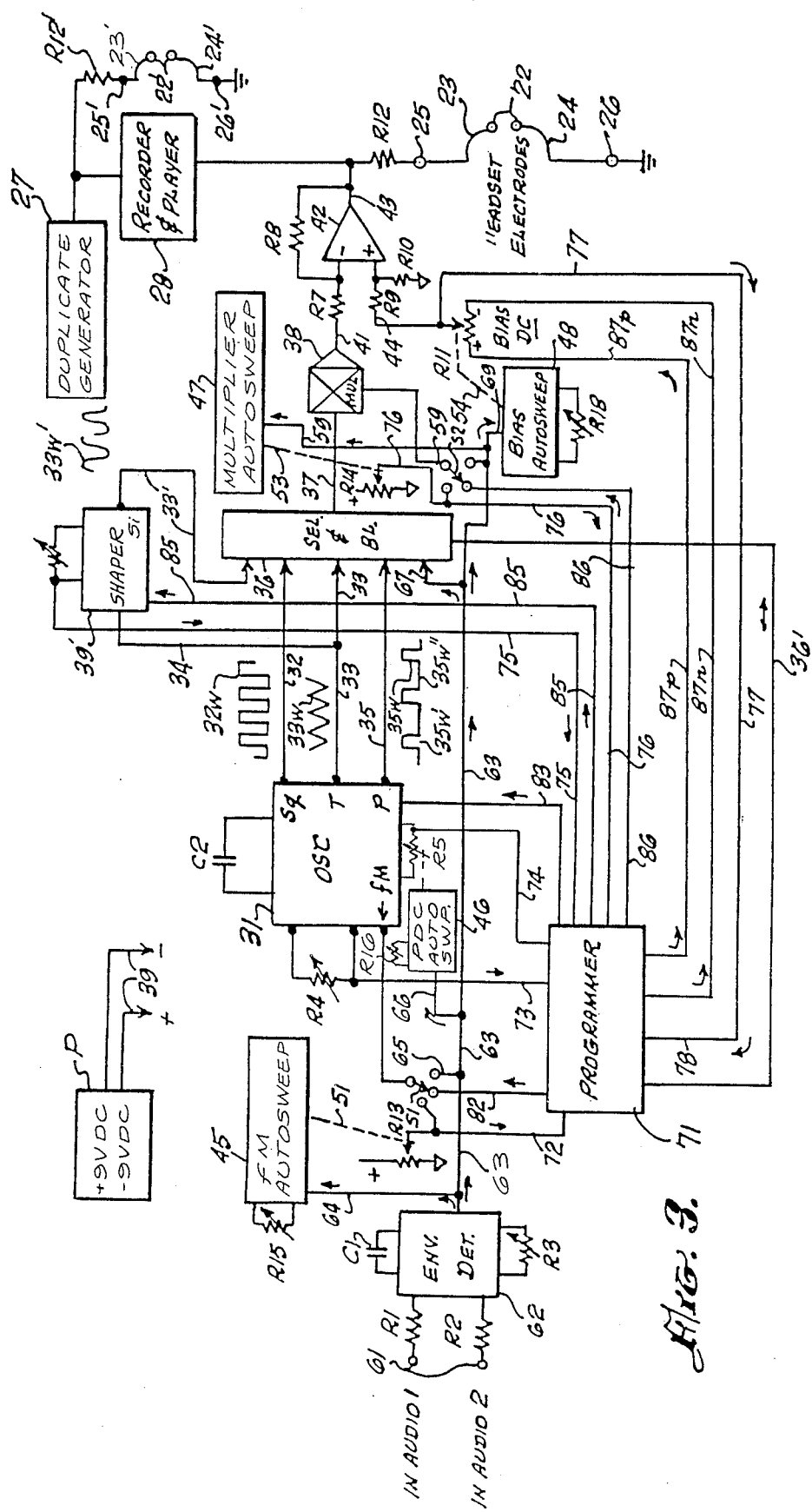
FIG. 3 is an electrical block diagram of an entertainment phosphene generator, with control-signal programming and phosphene-stimulus recording. This drawing illustrates the previously mentioned first through fourth embodiments of my invention. This drawing also illustrates apparatus usable in following the methods of the seventh and eighth embodiments of my invention.

Details of the wavetrain-producing apparatus 21 appear in FIG. 3. The apparatus 21 of FIG. 2 is represented by all of the components that appear in FIG. 3, with certain exceptions. The FIG. 3 components that are not part of the apparatus 21 are: the electrodes 22, leads 23 and 24, terminals 25 and 26, the duplicates 22' through 26' of these components (shown in the upper right-hand corner of the drawing), and the duplicate generator 27.

A suitable power supply P provides positive and negative supply voltages at 39 to all of the other components illustrated in FIG. 3. The power supply may consist of two nine-volt batteries, providing total isolation from any high-voltage sources for safety's sake.

At the heart of the wavetrain-producing apparatus is an oscillator 31 (FIG. 3), which generates basic square, triangle and pulse waveforms 32w, 33w and 35w at respective output terminals Sq, T and P. A ramp-shaped waveform (not illustrated) may also be provided at another output terminal. The pulse waveform 35w has "on" intervals 35w' and "off" intervals 35w". The fraction of the total cycle (the sum of the "on" and "off" intervals) that is occupied by the "on" interval is the so-called pulse duty cycle; this fraction may be adjusted between one tenth and nine tenths by manipulation—i.e., manual adjustment—of a rheostat R5 that is connected between two terminals of the oscillator 31.

The operating frequency of the oscillator 31 is set by a capacitor C2 (connected between two other terminals of the oscillator 31), in conjunction with a variable resistor R4 (also similarly connected to the oscillator 31). The frequency can be manually adjusted, between 0.1 and 50 Hz, by manipulation of the rheostat R4.

The operating frequency also can be varied or modulated by a voltage applied at the input terminal labeled "fm". A suitable source of such modulating voltage is available at the wiper of a potentiometer R13, across whose resistance there is applied a fixed excitation voltage. The excitation voltage is such that, as the wiper of this potentiometer is moved along the potentiometer resistance voltages in a suitable range for application to the "fm" terminal of the oscillator 31 appear at the wiper. The wiper is connected to the "fm" input terminal of the oscillator through a selector switch S1. When this switch S1 is set to connect the wiper to the "fm" input terminal, manual adjustment of the potentiometer wiper changes the frequency.

The sensitivity of the frequency to the two controls R4 and R13 just discussed may be substantially different, so that different effects are obtained by adjusting the two controls.

The triangle wave 33w is applied from its output terminal T through leads 33 and 34 to a shaper 39, which may be an integrator circuit, to produce an output signal 33w' (at an output terminal Si of the shaper) that is an approximation to a sine wave. A rheostat R6 connected to the shaper 39 permits manual variation of the symmetry of the sine wave.

All the wavetrains from the oscillator 31 and shaper 39 proceed along respective leads 32, 33, 35 and 33' to a selector and blender 36, which is in essence a selector switch. This switch 36, however, advantageously may be provided with the capability of "selecting" in the sense of combining two or more of the wavetrains, and the combining may be accomplished by blending the wavetrains in different proportions. Further, the individual, combined, or blended wavetrains may be "faded" into other individual, combined, or blended wavetrains. All these possibilities can be provided in ways that are generally well known to a person skilled in the art of routine production design of electronic circuits — such as operation-amplifier summing circuits.

The selected, combined, or blended output of the selector-blender 36 proceeds at 37 to a multiplier circuit 38. The multiplication applied in this circuit can be controlled by manipulation of the wiper of a potentiometer R14, from which suitable voltage can be directed through a lead 76 and a selector switch S2 to the multiplier 38. In this way the strength of the phosphenes can be controlled.

The multiplier output is directed through a coupling or summing resistor R7 to one input terminal "−" of a differential operational amplifier 42. The other input terminal "+" of the amplifier 42 receives a manually adjusted dc bias voltage from the wiper of a potentiometer R11, through another coupling or summing resistor R9. Bipolar excitation voltage is applied across this potentiometer R11, so that the entire output wavetrain of the amplifier 42 can be shifted toward either positive or negative voltages by manipulation of the wiper of the potentiometer R11. Additional resistors R10 and R8 are provided for proper bias and proper gain stabilization of the amplifier 42.

The output of the amplifier 42 passes at 43 to a current-limiting resistor R12, and through that resistor to one output terminal 25 of the apparatus. All signals are referred to circuit ground, so the other output terminal 26 of the apparatus is connected to circuit ground. Consequently, when the headset electrodes 22 are connected to the respective output terminals 25 and 26 as illustrated, the output voltage of the amplifier and current-limiting resistor R12 appears across the headset electrodes 22. A proportional stimulus current of course passes through the head of a person wearing the electrodes 22 as in FIGS. 1 and 2.

Now the foregoing description covers the essentially manual operation of the phosphene generator for entertainment purposes. Several semiautomatic and automatic features, however, remain to be presented.

The manual variation of oscillator frequency, as will be recalled, can be effectuated by manual manipulation of the wiper of a potentiometer R13 — provided that the switch S1 is set to connect that wiper to the "fm" input terminal of the oscillator 31. Now if the wiper is continuously moved along the potentiometer at a fixed rate, or in some other systematic fashion, the wiper voltage will change in a corresponding systematic way and the oscillator frequency will accordingly "sweep" through some range of values. Since there are many controls available to manual manipulation, the operator may not be able to manually move this potentiometer wiper on such a continuous basis.

It is possible for the operator to automatically accomplish the same result by turning on the "fm autosweep" module 45. FIG. 3 shows symbolically a mechanical linkage between the fm autosweep unit 45 and the wiper of the potentiometer R13, which is indeed one way — though a slightly cumbersome one — to automatically sweep the modulation voltage through a suitable range of values.

Manual manipulation of a rheostat R15 connected to the "fm autosweep" unit 45 controls the rate at which the autosweep unit sweeps the modulation voltage. Other adjustments (not illustrated) can control the range through which the voltage is swept, and can also control whether the sweep stops upon reaching one end of the range, or reverses, or resets quickly to the remote end of the range and then starts again, or follows some other protocol.

It will be understood, however, that as a matter of practical design the sweeping modulation voltage directed to the "fm" input terminal of the oscillator can be generated electronically within the fm autosweep unit 45. (There is then no need for a mechanical linkage 51 to move a mechanical wiper along a potentiometer winding as illustrated.) If desired, the fm autosweep unit 45 may have an internal oscillator of its own, to control the fm modulation voltage in a cyclical fashion. One satisfactory arrangement is to apply the output of the autosweep unit 45 across the potentiometer R13. The wiper setting will then pick off a fraction of the sweeping modulation voltage from the autosweep unit. The operator can use this fractional effect to scale down the frequency modulation produced by the autosweep unit 45. If the operator sets the rate-control rheostat R15 for zero sweep rate, then the potentiometer R13 receives constant excitation voltage and the system becomes essentially manual — like the system illustrated in FIG. 3.

Similarly the previously discussed pulse-duty-cycle control rheostat R5 can be automatically swept by a mechanical linkage 52 from a pulse-duty-cycle autosweep module 46, at a rate controlled by a sweep-rate control rheostat R16. Alternatively the pulse-duty-cycle autosweep module 46 may generate a sweeping voltage for application across a pulse-duty-cycle control potentiometer (not illustrated), whose wiper is connected to an input terminal of the oscillator 31 in place of one of the leads of the rheostat R5. If desired, the pulse-duty-cycle autosweep unit 46 may have an internal oscillator of its own, to control the pulse-duty-cycle modulation voltage in a cyclical fashion.

As in the analogous case of the alternative frequency-modulation system discussed in a preceding paragraph, the pulse-duty-cycle control potentiometer would pick off a fraction of the sweep voltage, permitting the operator to scale down the pulse-duty-cycle modulation produced by the pulse-duty-cycle autosweep unit 46. Also as in the case of the alternative frequency-modulation system, the duty-cycle autosweep could be set to zero sweep rate by suitable manipulation of the sweep-rate rheostat R16; the autosweep unit 46 would then apply a fixed voltage across the potentiometer and the duty-cycle modulation would be entirely manual — generally like the system illustrated in FIG. 3.

Similarly the wipers of the potentiometers R11 and R14 that control the dc bias and the multiplier circuit, respectively, can be placed under automatic control of a bias autosweep module 48 and a multiplier autosweep module 47. The sweep rates of these units are respectively controlled by manually adjusted control rheostats R18 and R17. The wipers of these two potentiometers R11 and R14 may be moved by respective mechanical linkages 54 and 53, as illustrated. Preferably, however, the autosweep units 48 and 47 can be made to generate sweeping voltages electronically, and these voltages can be applied across the respective potentiometers R11 and R14. If desired, these two autosweep units 48 and 47 may have internal oscillators of their own, to control the respective modulation voltages in a cyclical fashion. The wipers of these two potentiometers R11 and R14 then can be used to scale down the bias and multiplier automatic-sweep effects. The setting of the autosweep control rheostats R18 or R17 for a zero sweep rate will return these sweep systems to manual control, generally as illustrated.

It will be apparent that this additional level of automaticity gives the operator of the phosphene generator enormously greater capability to compose or improvise phosphenical effects of great complexity. In particular, if all of the autosweep units have their own independent oscillators, the operator of the device can control the effects at a very high level — namely, determining the frequencies, ranges and scale-down fractions of the sweep effects.

FIG. 3 illustrates, however, yet other levels of automatic capability to enhance the range of phosphenical sensations available through use of my invention.

A waveform-envelope detector circuit 62 accepts audio signal inputs from input terminals 61, through coupling resistors R1 and R2. The input terminals 61 may be connected to microphones and audio amplifiers, or to a tape or disc player or other playback device. In practice, such input devices may be made part of my phosphene generator or may be kept separate.

The envelope detector 62 has a characteristic time interval, set by a capacitor C1 and a manually variable resistor R3, over which it averages the amplitudes of the incoming audio signals. The purpose of this time averaging is to obtain a so-called waveform "envelope" voltage that varies more slowly than the audio signals themselves, and that therefore is useful for modifying the phosphene stimulus waveforms. As a general rule, such modifications are useful only if they are slow enough to produce perceptible phosphenes. (There is an exception to this rule, since as will be recalled from the earlier discussion of Oster's work, some beat effects can be invoked if there is more than one wavetrain generator in use.)

The waveform-envelope voltage is presented by the detector 62 to a signal bus 63, from which it can be tapped off as at 65 to a contact of the selector switch S1. The "fm" input terminal of the oscillator 31 can thus be made to receive the envelope voltage, instead of the manually adjusted or autosweep-adjusted voltage at the wiper of the fm control potentiometer R13.

With this setting, the frequency of the oscillator 31 varies in response to the music or other audio information entering the system at the input terminals 61. This responsiveness produces varieties of effects that are potentially far more interesting than the essentially repetitive effects available with the fm autosweep module 45 — provided, of course, that the selected audio information too is not essentially repetitive.

Similarly the waveform envelope voltage on the envelope bus 63 can be applied as at 64 to control the fm autosweep module 45, or as at 66 to control the duty-cycle sweep module 46, or as at 67 to set the selector/blender 36, or at 68 through switch S2 to adjust the multiplier 38, or at 69 to control the bias autosweep module 48. Switches (not shown) may be provided in the sweep modules to select one or any combination of these effects.

A phosphene composition or performance can be recorded for later playback, either by recording the actual headset voltages as in a tape recorder or digital recorder 28, or by recording the control signals as in a multichannel programmer 71, probably preferably digital.

If a tape recording system is preferred, the low-frequency signals may be applied to modulate a higher-frequency carrier, to effectively impress the signals onto the magnetic tape. This approach has the advantage that the phosphenic stimulus can be recorded on a tape track adjacent the corresponding music. A far simpler phosphene generator (having only the output amplifier 42, limiting resistor R12, and headset) can then be used to play back the musical and phosphenical composition.

On the other hand, the programmer approach has the advantage that the several control signals can later be modified or overridden independently, to modify the concert in relatively more subtle and sophisticated ways.

During recording, the programmer would receive a dozen or more input signals: the fm-sweep control signal as at 72 from the fm-sweep potentiometer wiper, the oscillator main frequency control signal as at 73 from the frequency control rheostat R4, the duty-cycle-sweep control signal as at 74 from the duty-cycle control rheostat R5, the pulse-shaper-asymmetry control signal as at 75 from the shaper control rheostat R6, several control signals from the selector/blender 36 along a signal bus 36', the multiplier-sweep control signal as at 76 from the multiplier control rheostat R17, and the bias-sweep control signal as at 77 from the bias control rheostat R11.

At playback the programmer would direct its own control signals as at 82, 83, 85, 86, 87p and 87n and 36' back to these same sweep units, duplicating the original effects. If desired any of the recorded control signals could be revised before playback.

Further, a skilled phosphene composer could enter a program directly at a keyboard on the programmer module 71 — even without going through the actuality of generating the stimulus wavetrains! This would require an advanced familiarity with the phosphenical sensations resulting from particular kinds of waveforms and from particular kinds of waveform control patterns. Such familiarity is analogous to a skilled music composer's familiarity with the musical sensations resulting from particular musical notes and from particular musical chords and phrases.

As elementary examples, a low-frequency sinusoidal wavetrain moves a phosphenic spot back and forth in the perceived visual field. A short-duration dc bias voltage similarly shifts the entire textured pattern produced by a higher-frequency signal. A static bias alone produces no sensation at all. If dc signals are applied for too long, they may have electrolytic effects on the eye and other neurologically active organs. These may be degrading to such organs, and should probably be avoided very carefully.

In consideration of the possibilities for exploiting beat patterns phosphenically, a duplicate phosphene generator 27, limiting resistor R12', and headset 23' through 26' may be provided as shown in FIG. 3. Of course the two sets of electrodes would have to be placed at somewhat different locations on the head. A common, two-track recorder/player module 28 can be attached to record and play back both sets of wavetrains.

Such a dual apparatus can also be useful for generation of controlled two-dimensional phosphenical effects. Such two-dimensional effects may be developed by placement of three or more electrodes at particular positions on a person's head, and energization of the electrodes in pairs from independent (or coordinated) wavetrain generators. Electrodes can be placed in a variety of places for a variety of effects — the bridge of the nose, the eyelids, and so forth.

Figure 4:
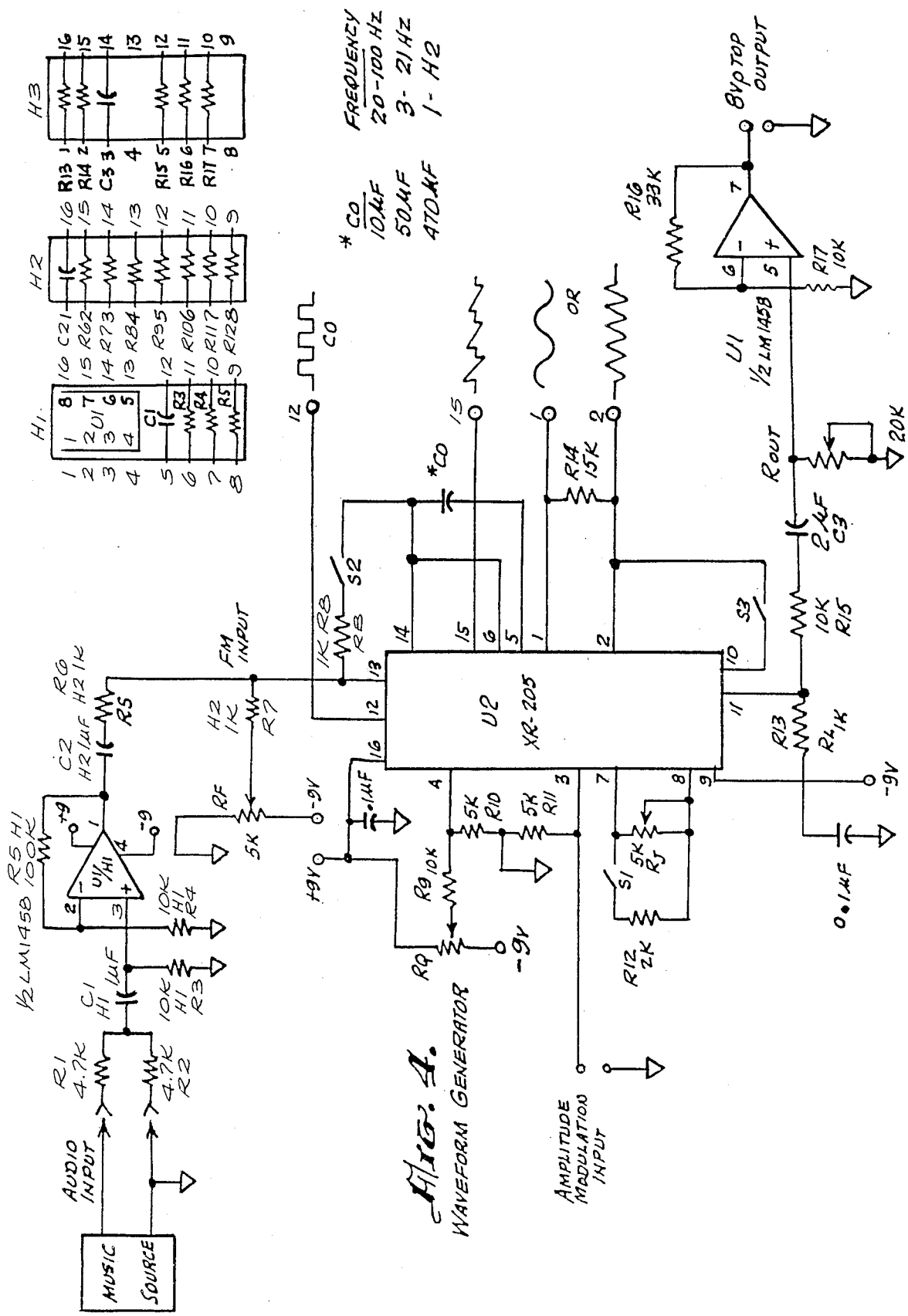
FIG. 4 is an electrical schematic of the key blocks (that is, those that are not essentially conventional) of the FIG. 3 embodiment.

The more-detailed schematic of FIG. 4 represents relatively simple forms of the key components of the FIG. 3 system — the oscillator, shaper, multiplier, selector/blender, and envelope detector. This drawing includes commercial component designator numbers, and shows suitable terminal numbers for some of the components. The block labeled "music source " is preferably a playback device, such as a small portable tape player, that can be carried easily on one's person.

Figure 5:
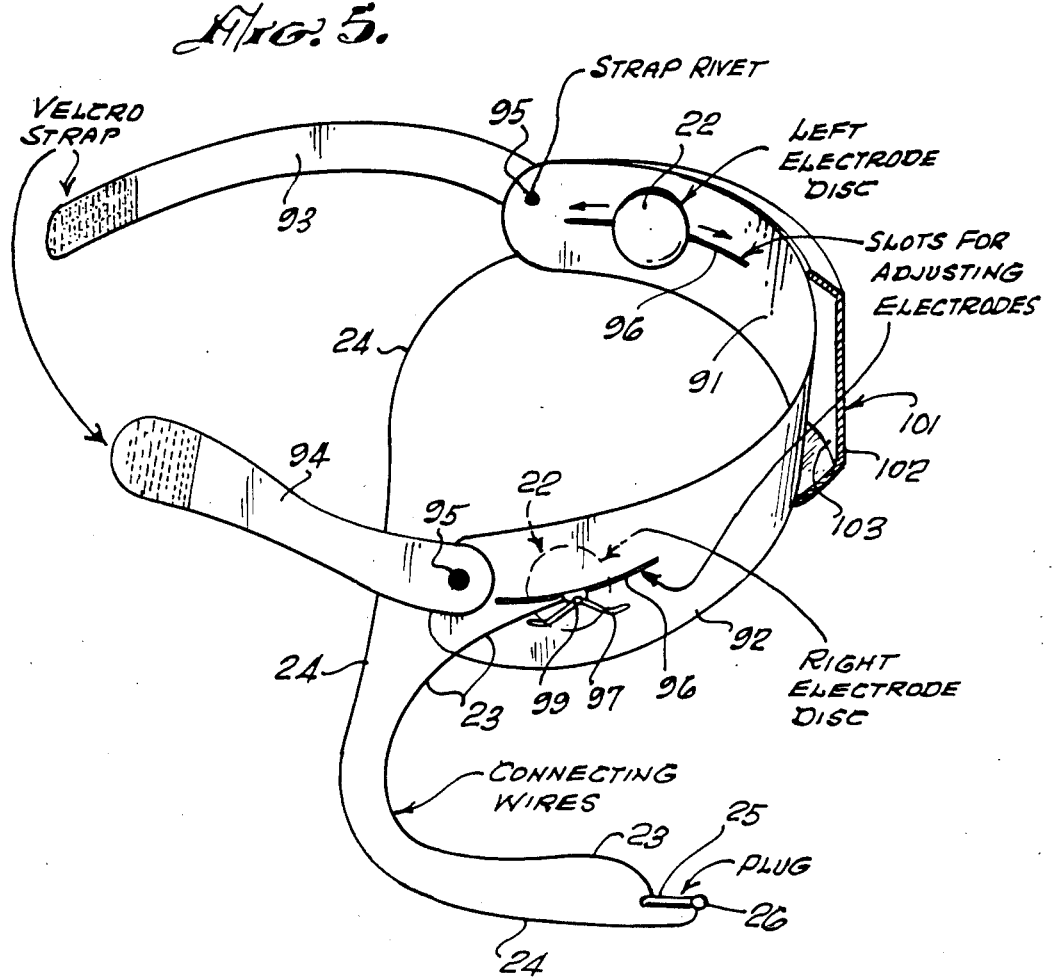
FIG. 5 is a generally perspective or isometric drawing, partly broken away, of a headset for use with the embodiments of FIGS. 1 through 4.

The headset, as shown in FIG. 5, has a curved inner plate 92 and a contoured outer cover 101 (drawn broken away at 102, to permit a better view of the parts between the plate 92 and cover 101). The plate 92 has two slits 96. The headset also has two convex electrode discs 22, preferably silver-plated for best skin contact, and each with a thin tab 99 (FIG. 6) extending from its rear surface through a respective one of the slits 96 in the plate 92.

A spring-steel wire 97 passes through a small hole in the end of each respective tab 99. The wire retains the tab 99 in the slot 96 and tends to hold the electrode disc 22 in a generally vertical orientation. This mounting arrangement, however, does permit the tab 99 to slide in the slot 96 for adjustment of the electrodes to accommodate different head sizes or produce different positional effects. My earlier headset designs using elastic bands with sewn-on electrode discs proved inadequate in adjustability.

Soldered to each tab 99 is a circuit wire 23 or 24, which in turn connects to one of the terminals 25 or 26 of an electrical connector. The inner surface of the cover 101 is spaced outwardly as at 103 from the plate 92 to allow space for the moving parts 99, 97, 23 and 24 of the electrode assemblies that protrude forwardly through the slots 96. (For some purposes this space can enclose all the electronics.) The electrical connector 25/26 is adapted to mate with the output connector of the phosphene generator as indicated in FIG. 3 (when the generator is not within the heatset).

Riveted as at 95 to the ends of the inner plate 92 are left and right head straps 93 and 94, terminating in "Velcro" fasteners to secure the headset to a user's head.

The headset has a dual purpose — screening out ambient light as well as supporting the electrodes. Accordingly it is desirable for the plate 92 and cover 101 to extend vertically somewhat above and (particularly) below the electrodes 22, to effectively block ambient illumination. Dark adaptation is important to the effective enjoyment of phosphenes, and darkened rooms may not always be available for such purposes.

Although FIG. 4 illustrates essentially analog circuitry, the ultimate in phosphene generators could well be based upon a microprocessor-and-software approach, placing the system operation under control of a program. Such a system, by virtue of its hardware simplicity, would also be capable of performing as the fifth embodiment of my invention, that which is directed to apparatus for aiding the blind — or as the sixth embodiment, directed to apparatus for two-dimensional scene presentation.

Figure 6:
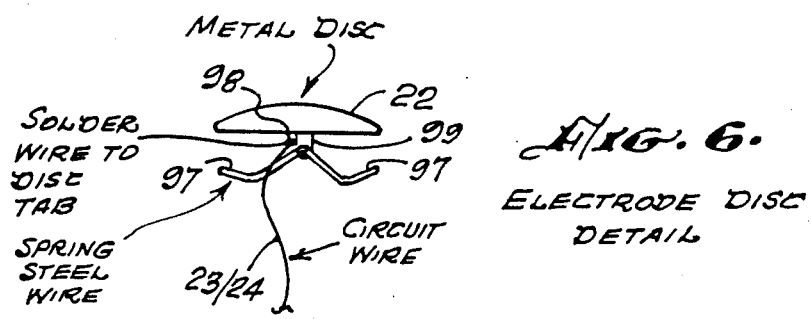
FIG. 6 is a plan drawing of the detail of each electrode assembly used in the FIG. 5 headset.
Figure 7:
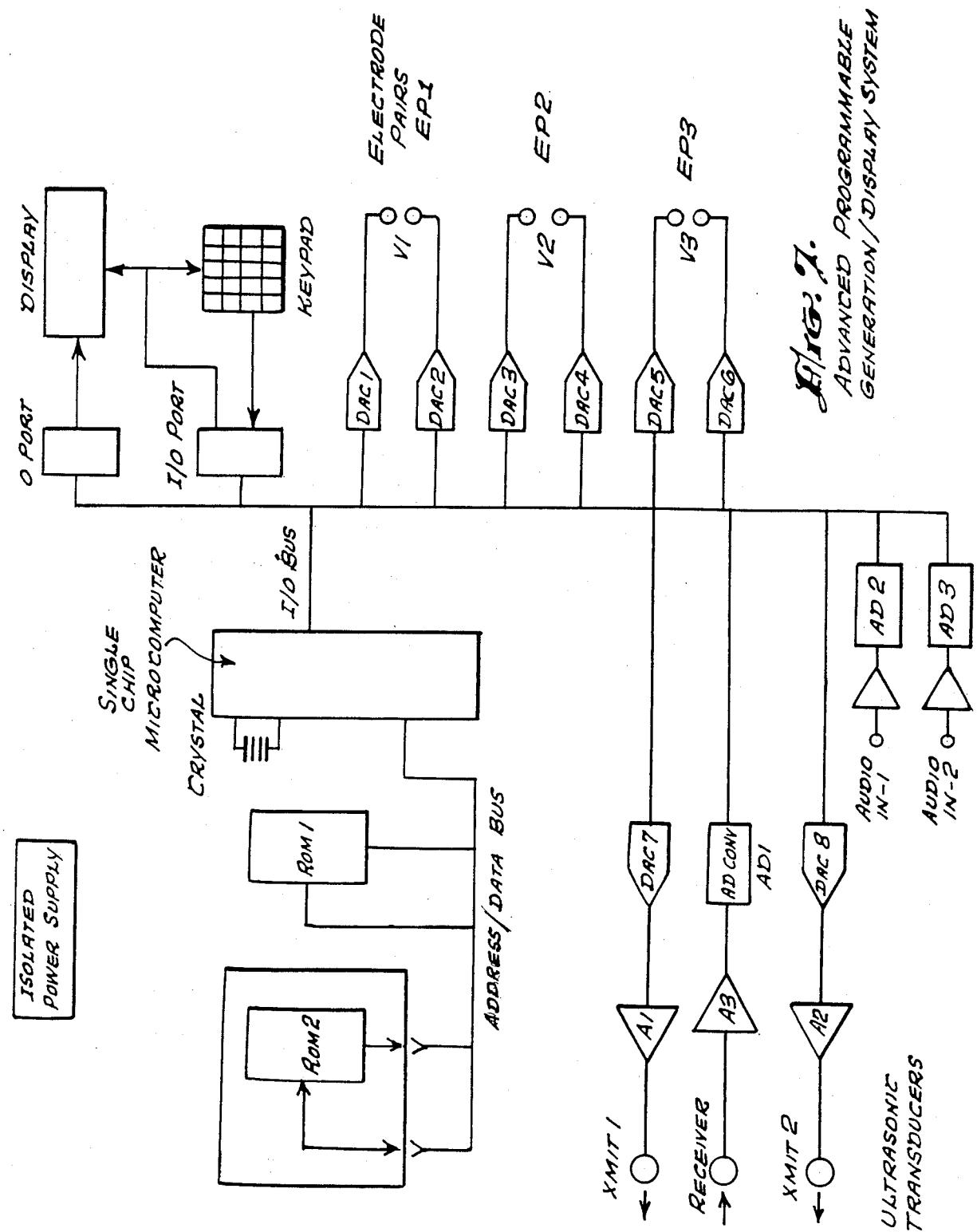
FIG. 7 is an electrical block diagram of a preferred embodiment of a phosphene generator using digital electronics controlled by a microcomputer — for use instead of the FIG. 3 embodiment.

FIG. 7 shows an electronic block diagram of a phosphene generator embodying a microprocessor-and-software approach, with three electrode sets. For one-dimensional effects the headset may be as illustrated in FIGS. 5 and 6. For two-dimensional effects the headset may be similar, but with one or more additional electrodes (about the size of those in FIGS. 5 and 6) placed on the bridge of the nose or on the forehead, cheeks or eyelids.

Another possibility for advanced two-dimensional effects is an array of very small silvered areas in a soft, flexible elastomeric pad — one for each eyelid. The silvered areas are individual electrodes, fed by conductors passed through the pads from a lightweight cable. As reported by Oster, op. cit. at 85, electrical stimulation of the eyelids induces phosphenes in the visual field at locations corresponding generally to the location of the stimulus relative to the eyelids. The exploitation of this phenomenon may be optimized for best "dimensional" sensations by some straightforward production-design work.

FIG. 7 includes many features that would make a phosphene generator of great power — in the sense of having the capability to produce an extremely large range of effects, and serve a variety of different purposes. It uses three analog-to-digital converters AD1 through AD3 to sample input signals. FIG. 7 also illustrates eight digital-to-analog converters DAC1 through DAC8, to produce output signals.

The heart of the device is a sixteen-bit, single-chip microcomputer system, such as the chip available commercially as an "Intel 8096." This unit includes a microprocessor, input and output (I/O) ports, address and data lines for external ROM (read-only memory) and/or RAM (read-and-write memory), internal clock timing oscillator, internal RAM, interrupts, timers, and all the necessary elements to make a powerful control system. These elements, considered individually, nowadays are entirely familiar to computer technicians and programmers who work in production design at a routine level.

The I/O bus in FIG. 7 connects the various digital-to-analog and analog-to-digital units to the control chip, and also interfaces to a keypad switch matrix — and, through an output port O, to an alphanumeric display. The keypad permits a user to select various operations, and the display informs the user of the operational status of the phosphene generator.

A main control program operating the keypad, display, and basic functions of the controller is contained in a thirty-two kilobyte read-only memory ROM1, permanently included in the system. Additional special functions, however, are contained in a program that resides in an auxiliary memory ROM2 — a plug-in read-only cartridge of up to sixty-four-kilobyte capacity. This cartridge can be changed as programs for new applications are developed for the generator.

Up to three electrode pairs (six electrodes in all) are driven by as many as six bipolar digital-to-analog converters, DAC1 through DAC6. The output voltage of each of these converters is controlled by the microprocessor and feeds (through a current-limiting resistance) an electrode pair. The voltage applied to the user by each electrode pair is the differential voltage between the outputs of each converter pair.

The digital-to-analog converter can produce complex waveforms under control of a program. Since phosphene frequencies are relatively low, the digital-to-analog converter "update rate" is relatively slow, and the sixteen-bit computer can easily compute output data for sine, square, pulse, triangle, ramp or other waveforms at each converter.

The control program can also maintain the software equivalent of twenty low-frequency waveform generators. By virtue of its "multiply" instructions, it can also effect amplitude or frequency modulation on any given output channel. In this way the apparatus can produce the complex waveforms which I (and future phosphene-generator operators, composers and programmers) have determined — and shall determine — produce specific phosphene effects.

The user will press specific function and numeric data keys on the keypad to obtain desired effects, or the control program in the auxiliary memory ROM2 will provide specific waveform sequences as in a composition — a "recorded" phosphene composition. The function and numeric keys will not necessarily be labeled in technical terms, any more than the keys on a piano are labeled with the frequencies of the corresponding notes. To the extent that labelling is considered appropriate in production units, verbal or symbolic representations of the types of effects created may be more appropriate than descriptions of the waveforms or electronic functions available.

As few as two of the output digital-to-analog converters may be used, in a simple performance, for electrode pairs on the temple. Two more pairs, however, permit four more electrodes to be located on the user — for elaborated spatial control of the phosphenes by the computer. The locations of the other pairs might be one electrode above each eye, and the other below each eye, for each additional pair. (Other variants have been discussed above.) My invention thus contemplates, for each eye independently, vertically as well as laterally directed phosphenes.

Two audio inputs from a stereo music source appear in FIG. 7. Each of these inputs is passed through an amplifier and signal conditioner to boost the low-level audio signal to five volts for input to an analog-to-digital converter AD2 or AD3.

From the resulting digital pulse trains the computer can extract a digital representation of each audio channel by sampling at a rate of twenty thousand samples per second (twenty kilohertz). From this digital data, various processing programs can extract envelope information as in the analog circuit of FIG. 3 — or, as may be preferred, frequency information, rhythm, or other parameters of the audio signal, for application to modulate the phosphene output voltages.

Turning now to the application of aiding blind people, the purpose of the components at left center in FIG. 7 will be explained. The two digital-to-analog converters DAC7 and DAC8 and the analog-to-digital converter AD1 are provided to interface with a sonar system that gathers information about objects in front of the blind user.

The user wears a version of the headset equipped with two ultrasonic transmitters XMIT 1 and XMIT 2 and with an ultrasonic receiver R. Although these units can be chest mounted, placing them on the user's head is preferred so that the user can obtain additional information in natural ways by tilting or turning of the head without necessarily moving the torso. All the necessary transmitter, receiver, and other phosphene-generator electronics may be mounted within the headset cover 101.

The receiver signal is amplified and filtered by an operational amplifier A3 and fed to the corresponding analog-to-digital converter AD1. The two transmitters are fed from the separate analog-to-digital converters DAC7 and DAC8 via amplifiers A1 and A2. The computer can create a digital excitation for each transmitter independently.

The computer generates a sonar "chirp" pattern at one transmitter XMIT1 and "listens" for the echo with the receiver R. The computer can time the propagation of the wave from one transmitter XMIT1 (at, say, the left-hand side) to a reflecting object in the field of the transmitter-sensor system and back to the receiver sensor R. Then by "chirping" the other transmitter XMIT2 (at, say, the right-hand side), again listening for the echo, and timing the propagation, the computer collects enough information to calculate the range and bearing of the reflecting object.

Figure 8:
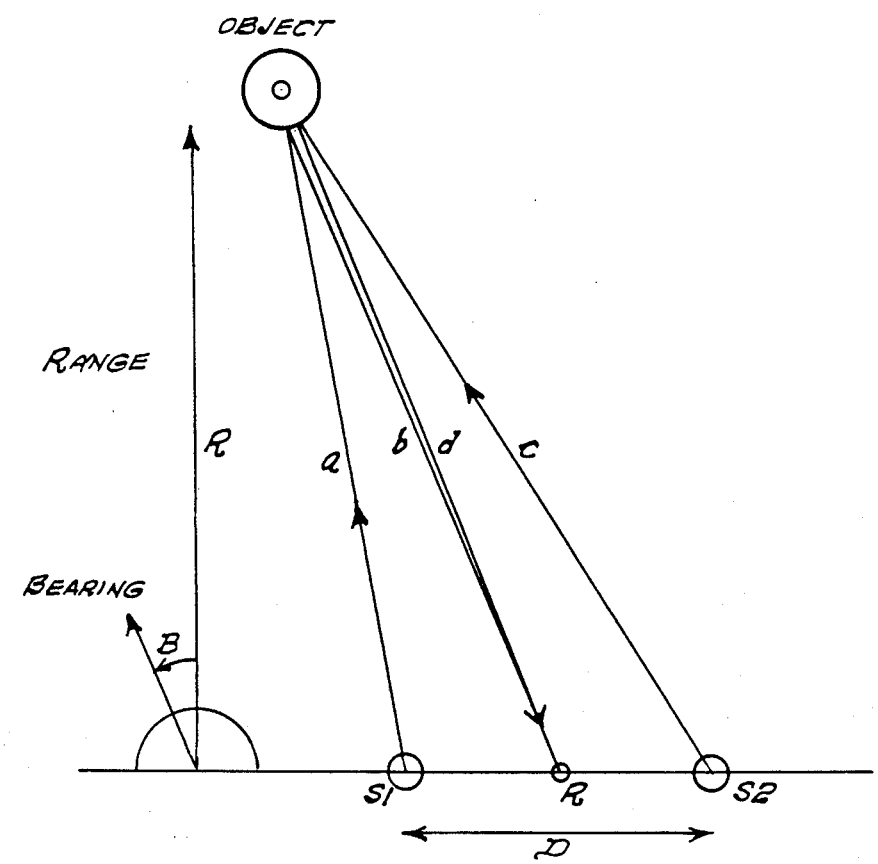
FIG. 8 is a diagram showing the interrelationship of certain parameters of interest in effectuating the operation of the FIG. 7 system to aid the blind.

This data-collection and calculation process is diagrammed in FIG. 8, where the transmitters are represented as sources S1 and S2. The propagation of the "chirp" from source S1 to the receiver R follows a two-stage sonar signal path a-b, and the propagation from source S2 to the receiver R follows a similar path c-d. Given the distance D that separates the sources S1 and S2, and the fact that the receiver is midway between them, the computer can calculate the range R and bearing angle B of the object O. This calculation requires a program using well-known trigonometric procedures to solve the triangles in the diagram.

Alternative data-collection stages may use a video-like camera, as previously mentioned, or any of various other ranging and angling detection systems known in the targeting or related arts.

The computer can further be programmed to use this information to construct a driving waveform for, say, the electrode pair EP1. Using the digital-to-analog converters DAC1 and DAC2 to form a bipolar source, the program can produce a phosphene spot or other pattern with the apparent bearing of the target object. This process requires calculation of the proper polarity and magnitude of voltage required at each electrode to produce the proper dc bias value, and a brief pulsing of the calculated voltages.

The pulse duration or the voltage amplitude, or both, can be used to control the brightness of the phosphene. For example, a short pulse can be used to produce a faint sensation indicating a relatively remote object, or a longer pulse to produce a bright sensation indicating a closer object. Since the computer can control the apparent bearing of the sensation through adjustment of the "phase" voltage between the electrodes, the computer is free to scale the pulse duration or voltage up and down without disturbing the apparent bearing.

Apparent bearing and brightness are not the only practical "codings" of actual bearing and distance. Innumerable other range-and-bearing codings of the sensation, as suggested above, can be used instead — as may be preferred by the individual blind user, or by medical vision prostheticists who will be schooled in such matters.

It will be understood that not all blind people possess the neural mechanisms near the normal retinal region to respond to my phosphene generator. Those genetically or otherwise congenitally impaired, and those blinded by degenerative neural disease or trauma to the entire eye, may not be able to make use of my invention at all. Individuals affected by cataracts or other essentially "optical" malfunctions, however, are better situated These individuals may be expected usually to have retained the retinal structure and attached nerve pathways that are the naturally occurring mechanisms for transmission of phosphene stimuli to the optical center of the brain.

To the extent that there are people in intermediate categories of impairment — for example, suffering from deterioration of the optical nervous system that is only partial — various relatively obscure "codings" may be extremely important. The relatively intuitive codings already discussed may be unusable by such people. For such individuals, phosphene codings to the range and bearing that are not at all intuitive may be usable, though requiring extensive training of the user. These codings therefore may be far more important than might at first be supposed.

Such different codings, including but not limited to the use of color, texture, directionality, degree of asymmetry or other shape parameters, and even specific positional distinctions — any of which may be painstakingly customized to the individual user's specific residual of unimpaired neural capacity — are all within the scope of my invention.

My invention also contemplates using the advanced phosphene generator of FIG. 7 to trace a phosphene spot in a raster-like pattern. Phasing of the voltage V1 to the first electrode pair EP1 addresses the apparent horizontal position of a phosphene spot, while voltages V2 and V3 address the apparent vertical position.

Though relatively slow sweep rates are seemingly required, by amplitude modulation of the three voltages the phosphene spot can be varied in brightness as it moves across the raster. In a manner similar to intensity modulation of an electron beam in a cathode ray tube, a specific image of a geometric pattern or a scene may thus be formed.

Reported phosphenical sensitivity to beats, as in Oster's work, also calls attention to the fact that the receiving neurons are not necessarily totally insensitive to higher-frequency waveforms. I do not know at what stage, along the retina-to-brain pathway, high-frequency signals are rejected. It seems quite possible that a carefully stabilized high-frequency raster is not rejected, provided that — for example — each individual point in the visual field is "strobed" (stimulated) at a low frequency. For example, a hundred-line raster that repeats thirty-five times per second has the effect of strobing each point at only 35 Hz, though the horizontal deflection voltage runs at a hundred times this frequency — namely, at 3.5 kHz.

Operation of a scene-presentation system in this way would not be in the least limited with respect to rapidity of scene motion, since the normal visual apparatus cannot follow motion corresponding to frequencies above about 35 or 40 Hz anyway. The necessity to avoid stimulating each point more often than about thirty-five times per second, however, may require use of a raster that is relatively coarse. The reason for this possible limitation is that each independently stimulable "point" may turn out to be relatively large, in terms of the fraction of the apparent visual field to which it corresponds.

It is to be understood that all of the foregoing detailed descriptions are by way of example only, and not to be taken as limiting the scope of my invention — which is expressed only in the appended claims.

I claim:

1. A programmable phosphene generator, requiring no intracranial implant, for producing visual sensations in a person; said generator comprising:
    means for generating a voltage wavetrain that is variable and for responding to control signals to vary the voltage wavetrain;
    means, responsive to external inputs, for generating substantially continuously varying control signals, to control the voltage-generating means to substantially continuously vary the wavetrain;
    means for applying the control signals from the control-signal generating means to the wavetrain-generating means;
    means for storing and later playing back the control signals; and means for applying the wavetrain to the outside of such a person's head.

2. A programmable phosphene generator, requiring no intracranial implant, for producing visual sensations in a person; said generator comprising:
- means for generating a voltage wavetrain that is variable and for responding to control signals to vary the voltage wavetrain;
- external inputs that comprise manually operated handles or the like;
- means, responsive to the external inputs, for generating substantially continuously varying control signals, to control the voltage-generating means to substantially continuously vary the wavetrain;
- means for applying the control signals from the control-signal generating means to the wavetrain-generating means;
- means for storing and later playing back the control signals; and
- means for applying the wavetrain to the outside of such a person's head.

3. A programmable phosphene generator, requiring no intracranial implant, for producing visual sensations in a person; said generator comprising:
- means for generating a voltage wavetrain that is variable and for responding to control signals to vary the voltage wavetrain;
- at least one eternal input that comprises a source of electrical signals derived from music;
- means, responsive to the external inputs, for generating substantially continuously varying control signals, to control the voltage-generating means to substantially continuously vary the wavetrain;
- means for applying the control signals from the control-signal generating means to the wavetrain-generating means;
- means for storing and later playing back the control signals; and
- means for applying the wavetrain to the outside of such a person's head.

* * * * *